United States Patent [19]
LeGrow et al.

[11] Patent Number: 5,932,231
[45] Date of Patent: Aug. 3, 1999

[54] HIGH PURITY BRANCHED ALKYLSILSESQUIOXANE FLUIDS

[75] Inventors: Gary E. LeGrow, Newberry; William I. Latham, III, Gainesville, both of Fla.

[73] Assignee: PCR, Inc., Gainesville, Fla.

[21] Appl. No.: 08/893,439

[22] Filed: Jul. 11, 1997

[51] Int. Cl.$^6$ ........................................................... A61K 7/00
[52] U.S. Cl. .................... 424/401; 424/70.1; 424/70.12; 424/70.121
[58] Field of Search .............................. 424/401, 70.121, 424/70.12, 70.1

[56] References Cited

U.S. PATENT DOCUMENTS

| | | | |
|---|---|---|---|
| 3,978,104 | 8/1976 | Razzono | 260/448 |
| 4,206,289 | 6/1980 | Meiiners et al. | 521/110 |
| 4,281,147 | 7/1981 | Koerner et al. | 556/459 |
| 4,985,342 | 1/1991 | Muramoto | 430/280.1 |
| 5,039,518 | 8/1991 | Barone et al. | 424/63 |
| 5,179,185 | 1/1993 | Yamamoto et al. | 528/32 |
| 5,679,822 | 10/1997 | Legrow | 556/456 |

FOREIGN PATENT DOCUMENTS 1050915  10/1963  United Kingdom .

OTHER PUBLICATIONS

Epstein, Frederick, Low–Polymeric Branched Monoaryl Siloxanes, CA Chemical Abstracts, vol. 55 17579i, Oct. 1958.

Sheldon Buckler, Tris Subdtituted Carbamoyl Phosphines vol. 45 10676 d–e. Chemical Abstracts, Jan. 1961.

James Hyde, Organopolysiloxanes Prepared by the Reactionof Salts of Silanols with Halosilanes, Sep. 1951.

Cosmetic Ingredient Dictionary, Monographs p. 757–See Phenyl Trimethicone.

CTFA International Buyers Guide, Ingredients and Suppliers, p. 166 See Phenyl Trimethicone.

Information about Cosmetic Ingredients, see Dow Corning 556, 1983.

Primary Examiner—Thurman K. Page
Assistant Examiner—D. Faulkner
Attorney, Agent, or Firm—Hedman, Gibson & Costigan, P.C.

[57] ABSTRACT

The invention provides high purity branched alkylsilsesquioxane containing fluids of the general formula $Me_3SiO—(Me_3SiORSiO)_x—SiMe_3$, wherein Me is methyl, R is a monovalent hydrocarbon substituent, and x is 1 to 6, and an essentially zero waste process for their synthesis in quantitative yield; and especially n-octylsilsesquioxane containing fluids which are structural analogs of phenylsilsesquioxane containing fluids of the general formula $Me_3SiO—(Me_3SiOPhSiO)_x—SiMe_3$, wherein Me is methyl, Ph is phenyl, x is 1 to 6, and have substantially identical sensory properties to their phenylsilsesquioxane counterparts.

22 Claims, 1 Drawing Sheet

HIGH PURITY BRANCHED ALKYLSILSESQUIOXANE FLUIDS

FIELD OF THE INVENTION

The present invention relates to high purity branched alkylsilsesquioxane containing fluids and a method for their preparation. More specifically, the present invention relates to neutral branched octylsilsesquioxane fluids which are substantially free of impurities.

As used throughout the present specification, the abbreviation Me stands for methyl and the abbreviation Ph stands for phenyl.

BACKGROUND OF THE INVENTION

Phenyl-containing silicone polymers with high refractive indices are known to have some dimethylsiloxane-like properties, organic compatibility and chemical stability to strong media.

Phenylsilsesquioxane fluids are useful for incorporation into cosmetic formulations, without any chemical reactions, to provide silicone benefits without emulsification. An example of such a use is described in Barone et al., U.S. Pat. No. 5,039,518.

In a previously filed U.S. patent application Ser. No. 08/789,277, a significant advance in the state of the art of neutral branched phenylsilsesquioxane fluids was disclosed wherein the compounds were prepared with substantially no detectable silanol (SiOH), substantially no alkoxysilane (SiOR) where R is a monovalent hydrocarbon substituent, substantially no detectable chlorosilane, and substantially no free organic and inorganic compounds present.

Alkyl-containing silicone polymers typically have somewhat lower refractive indices than their corresponding phenyl-containing silicone analogs; however, they do exhibit organic compatibility and chemical stability to strong media. Branched alkylsilsesquioxane polymers are not known wherein the alkyl group ranges from hexyl to tetradecyl. Furthermore, the utility of these compounds in applications such as disclosed in U.S. Pat. No. 5,039,518 are not known.

Additionally, it is well known that the phenylsilsesquioxane polymers break down into benzene and phenols after use of the cosmetic products into which they are incorporated. Such compounds are detrimental to the environment. Accordingly, the development of a replacement for the phenysilsesquioxane polymers which does not have the environmental drawback of breaking down to benzene and phenol would solve a long felt need in the art. Such a need is met by the alkylsilsesquioxane compounds of the present invention which break down to environmentally friendly carbon dioxide and water.

It is noted here that hexylsilsesquioxane monomer was disclosed in J. Chem. Soc. (Dalton Transactions) 3127 (1994) as synthesized by platinum catalyzed hydrosilylation of hexene-1 by HSi(OSiMe$_3$)$_3$. No yield or purity for this reaction is reported. Also United Kingdom Patent No. 1,426,783 describes a hexylsilsesquioxane monomer and a tetradecylsilsesquioxane monomer prepared by a synthesis process in the absence of added water with low yield and a tertiary amyl chloride by-product. Thus, neither prior art process describes preparing polymeric alkylsilsesquioxanes, nor do they describe processes to produce the alkylsilsesquioxane at high purity.

SUMMARY OF THE INVENTION

The present invention provides a high purity branched alkylsilsesquioxane fluid of the general formula Me$_3$SiO—(Me$_3$SiORSiO)$_x$—SiMe$_3$ wherein Me is methyl, R is a straight chain or branched chain monovalent hydrocarbon substituent with from 6 to 14 carbon atoms, and x is from 1 to about 6 and wherein the alkylsilsesquioxane fluid is substantially free of alkoxysilanes, chlorosilanes, silanol functionalities, and free of organic and inorganic compounds.

The present invention also provides a method for producing high purity branched alkylsilsesquioxane fluids, the process comprising the steps of (i) hydrolyzing a mixture of pure trimethylchlorosilane and pure alkyltrichlorosilane with sufficient water to produce a reaction mixture of a silicone reaction intermediate and an aqueous layer not in excess of 25 weight percent hydrochloric acid, at a temperature of up to 90° C.; (ii) washing residual acid from the aqueous layer; (iii) azeotropically removing water from the silicone reaction intermediate; and (iv) trimethylsilylating the silanol groups in the silicone reaction intermediate in the presence of at least a stoichiometric amount of hexamethyldisiloxane and an acid catalyst.

DETAILED DESCRIPTION OF THE PRESENT INVENTION

Figure 1:
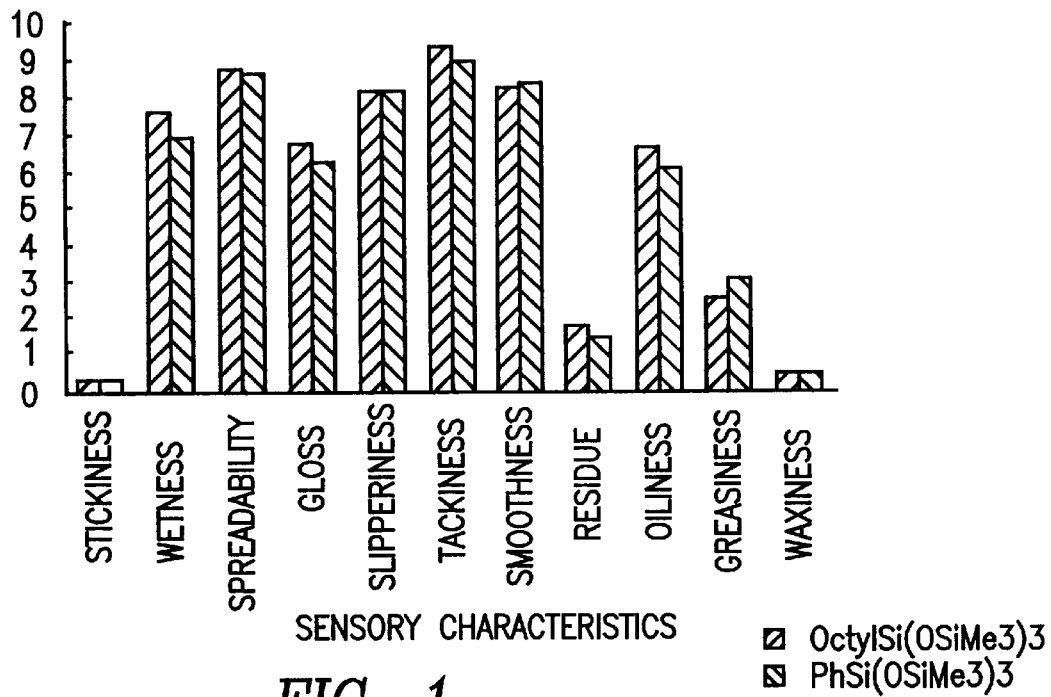
FIG. 1 depicts in bar graph form a sensory comparison of a branched alkylsilsesquioxane of the present invention with an analogous phenylsilsesquioxane.

The present invention provides a novel branched alkylsilsesquioxane fluid of the general formula:

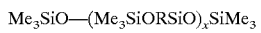

Me$_3$SiO—(Me$_3$SiORSiO)$_x$SiMe$_3$ wherein Me is methyl, R is a straight chain or branched chain monovalent hydrocarbon substituent of from 6 to about 14 carbon atoms, and x is from 1 to about 6, which fluid is characterized in that it is substantially, and preferably completely, free of detectable amounts of silanol, alkoxysilane, chlorosilane, and other organic and inorganic impurities.

For example R may comprise an alkyl group having from 6 to 14 carbon atoms such as but not limited to hexyl, n-hexyl, i-hexyl, heptyl, n-octyl, i-octyl, nonyl, decyl, dodecyl, tetradecyl and the like, or it may comprise any other monovalent hydrocarbon substituent known to those of ordinary skill in the art. Additionally, it is contemplated herein that each R may be the same or different monovalent hydrocarbon substituent.

The high purity branched alkylsilsesquioxane fluids of the present invention can be prepared by a novel two step process. In the first step, a mixture of trimethylchlorosilane and monovalent hydrocarbon substituted trichlorosilane, such as an alkyltrichlorosilane, preferably n-octyltrichlorosilane, in a molar ratio ranging from about 5:1 to about 1:1 are hydrolyzed with a stoichiometric excess of distilled water which produces an aqueous layer not exceeding 25 weight percent, preferably less than 18 weight percent, of hydrochloric acid.

The trimethylchlorosilane and monovalent hydrocarbon substituted trichlorosilane reactants are available commercially or may be produced by methods known to those skilled in the art. In a preferred embodiment, substantially pure to completely pure reactants are employed in the process of the present invention. In an especially preferred embodiment pure n-octyltrichlorosilane is employed as the monovalent hydrocarbon substituted trichlorosilane reactant.

The co-hydrolysis reaction of the first step of the method of the present invention may be carried out over a range of temperatures of from about ambient to about 90° C., preferably from about ambient to about 80° C., and more preferably from about ambient to about 60° C. The reactor is preferably also equipped with a cold water condenser, capable of preventing the loss of any volatile silane species, including but not limited to trimethylchlorosilane.

After the co-hydrolysis reaction is complete, the acid layer is separated from the silicone layer.

The silicone layer is washed free of residual acid, by any of the methods known to those of ordinary skill in the art. The silicone layer is then heated to 100° C., at which point water and hexamethyldisiloxane co-volatilize. Free water is then azeotropically removed from the silicone layer.

Hexamethyldisiloxane which has volatilized is returned to the silicone layer after substantially all of the free water has been removed.

At this stage of the process the chemical composition of the silicone layer can be described by the following general formula:

wherein Me is methyl, R is a monovalent hydrocarbon substituent alkyl having from 6 to 14 carbon atoms, x is from 0 to 6, and y is from 0 to 6. This includes species wherein both x and y are 0, i.e., species of the formula $Me_3SiOSiMe_3$, or hexamethyldisiloxane, which is present as a result of homo-hydrolysis of trimethylchlorosilane, as opposed to the co-hydrolysis of trimethylchlorosilane and alkyltrichlorosilane. Hexamethyldisiloxane is a necessary reactant for the second step of the process of the present invention.

In the second step of the process of the present invention, the silicone layer, at ambient temperature, is catalyzed with an acidic catalyst, such as 0.1% by weight of trifluoromethanesulfonic acid. Other catalysts contemplated for use in the present invention are any of the non-chlorine containing acids such as sulfuric acid and nitric acid.

The silicone layer is then stirred and heated up to about 50° C. for a sufficient time to replace all residual SiOH (silanol) groups with $SiOSiMe_3$ groups. The completion of this reaction may readily be monitored by gas layer chromatography as is well known to those of ordinary skill in the art.

After completion of the reaction, the acid catalyst is neutralized with a base or salt, and the salt formed is filtered from the reaction mixture. A wide variety of bases and salts may be employed to neutralize the acid. Exemplary of the salts useful in the practice of the present invention are magnesium sulfate, calcium carbonate, calcium bicarbonate and the like. The remaining silicone material is then stripped to remove any residual hexamethyldisiloxane to provide the high purity branched alkylsilsesquioxane containing fluids of the present invention.

In an especially preferred embodiment, a wide range of branched trimethylsilylated n-octylsilsesquioxane fluids can be produced in accordance with the present invention with refractive indices ranging from below about 1.4100 (25° C.) to greater than about 1.4400 (25° C.), with corresponding viscosities ranging from about 5.0 cs (25° C.) to greater than about 500 cs (25° C.) by varying the molar ratio of trimethylchlorosilane to n-octyltrichlorosilane.

In an especially preferred embodiment, the residual hexamethyldisiloxane removed in the stripping step of the second process step of the present invention may be recycled to the initial reaction mixture. In such an embodiment, the amount of trimethylchlorosilane in the initial reaction mixture is reduced by the amount of hexamethyldisiloxane recycled, with a corresponding decrease in the amount of distilled water needed for hydrolysis and to maintain the hydrochloric acid concentration in the acid layer constant. In this manner, the present invention further provides a process which is essentially a zero waste process with respect to organosilicon chemicals.

DESCRIPTION OF THE PREFERRED EMBODIMENTS

The following examples illustrate the present invention. They are not to be construed to limit the scope of the appended claims in any manner whatsoever.

EXAMPLE 1

From an addition funnel, a mixture of 271.3 g (2.5 mole) of pure trimethylchlorosilane and 247.5 g (1.0 mole) of n-octyltrichlorosilane was slowly added, with stirring, to a 2 liter 3 necked round bottom flask equipped with a mechanical stirrer, thermometer, nitrogen overgas, condenser and heating mantel, containing 964 g (53.5 mole) of distilled water. The rate of addition of the chlorosilane mixture was controlled to prevent the temperature of the reaction mixture from exceeding 60° C. After the addition was complete, the contents of the flask were allowed to cool to 40° C. The lower aqueous layer was removed from the flask and 1000 g of distilled water were introduced and rapidly stirred and mixed with the upper silicone layer to reduce its acid content. The stirrer was stopped and the two layers were allowed to separate, whereupon the lower acid layer was again removed. This water washing operation was repeated two more times until the pH of the upper layer was in excess of 6. The silicone layer was then heated to 100° C. causing hexamethyldisiloxane and water to co-distill. Water was azeotropically removed from the silicone fluid in this manner until no more water was formed. The hexamethyldisiloxane was returned to the flask. To the flask was added 3.3 g of sulfuric acid with stirring. The contents of the flask were then heated to 50° C. and held at that temperature for 1 hour. After cooling to room temperature a sample of the silicone fluid was analyzed by GC which showed the absence of SiOH containing species. The acid in the system was neutralized by washing the product with 1000 g of an aqueous sodium bicarbonate solution, followed by water washing with distilled water to remove salts. The silicone layer, which at this point weighed 350 g (95% theory) was then heated at 100° C. at a pressure of 30 mm Hg vacuum to remove water and hexamethyldisiloxane.

The clear, colorless, odorless product weighed 315 g (86% theory) had a refractive index of 1.420 (25° C.), a density of 0.875 g/ml and a viscosity of 20.3 cP (25° C.). as layer chromatography analysis of this material identified 51% tris(trimethylsiloxy)n-octylsilane, 23% tetrakis (trimethylsiloxy)-1,3,-di-n-octyldisiloxane, 11% pentakis (trimethylsiloxy)-1,3,5-tri-n-octyltrisiloxane and 15% higher oligomers.

EXAMPLE 2

From an addition funnel, a mixture of 108.5 g (1.0 mole) of pure trimethylchlorosilane and 247.5 g (1.0 mole) of n-octyltrichlorosilane was slowly added, with stirring, to a 2 liter 3 necked round bottom flask equipped with a mechanical stirrer, thermometer, nitrogen overgas, condenser and heating mantel, containing 701 g (38.9 mole) of distilled water. The rate of addition of the chlorosilane mixture was controlled to prevent the temperature of the reaction mixture from exceeding 60° C. After the addition was complete, the contents of the flask were allowed to cool to 40° C. The lower aqueous acid layer was removed from the flask and 700 g of distilled water were introduced and rapidly stirred and mixed with the upper silicone layer to reduce its acid content. The stirrer was stopped and the two layers were allowed to separate, whereupon the lower acid layer was again removed. This water washing operation was repeated two more times until the pH of the upper layer was greater than 6. The silicone layer was then heated to 100° C. causing hexamethyldisiloxane and water to co-distill. Water was azeotropically removed from the silicone fluid in this manner until no more water was formed. The hexamethyldisiloxane was returned to the flask. To the flask was added 2.0 g of sulfuric acid with stirring. The contents of the flask were then heated to 50° C. and held at that temperature for 1 hour. After cooling to room temperature a sample of the silicone fluid was analyzed by GC which showed the absence of SiOH containing species. The acid in the system was neutralized by washing the product with 1000 g of an aqueous sodium bicarbonate solution, followed by water washing with distilled water to remove salts. The silicone layer, which at this point weighed 245 g (99% theory) was then heated at 100° C. at a pressure of 30 mm Hg vacuum to remove water and hexamethyldisiloxane.

The clear, colorless, odorless product weighed 230 g (94% theory) and had a refractive index of 1.433 (25° C.), a density of 0.853 g/ml and a viscosity of 34.9 cP (25° C.).

Gas layer chromatography analysis of this material identified 43% tris(trimethylsiloxy)n-octylsilane, 20% tetrakis (trimethylsiloxy)-1,3-di-n-octyldisiloxane, 17% pentakis (trimethylsiloxy-1,3-5,tri-n-octyltrisiloxane and 20% higher oligomers.

EXAMPLE 3

From an addition funnel, a mixture of 272 g (2.5 mole) of pure trimethylchlorosilane and 124 g (0.5 mole) of n-octyltrichlorosilane was slowly added, with stirring, to a 2 liter 3 necked round bottom flask equipped with a mechanical stirrer, thermometer, nitrogen overgas, condenser and heating mantel, containing 465 g (25.8 mole) of distilled water. The rate of addition of the chlorosilane mixture was controlled to prevent the temperature of the reaction mixture from exceeding 60° C. After the addition was complete, the contents of the flask were allowed to cool to 40° C. The lower aqueous layer was removed from the flask and 500 g of distilled water were introduced and rapidly stirred and mixed with the upper silicone layer to reduce its acid content. The stirrer was stopped and the two layers were allowed to separate, whereupon the lower acid layer was again removed. This water washing operation was repeated two more times until the pH of the upper layer was greater than 6. The silicone layer was heated to 100° C. causing hexamethyldisiloxane and water to co-distill. Water was azeotropically removed from the silicone fluid in this manner until no more water was formed. The hexamethyldisiloxane was returned to the flask. To the flask was added 1.0 g of sulfuric acid with stirring. The contents of the flask were then heated to 50° C. and held at that temperature for 1 hour. After cooling to room temperature a sample of the silicone fluid was analyzed by GC which showed the absence of SiOH containing species. The acid in the system was neutralized by washing the product with 500 g of an aqueous sodium bicarbonate solution, followed by water washing with distilled water to remove salts. The silicone layer, which at this point weight 260 g (86% theory) was then heated at 100° C. at a pressure of 30 mm Hg vacuum to remove water and hexamethyldisiloxane.

The clear, colorless, odorless product weighed 128 g (42% theory) and had a refractive index of 1.415 (25° C.), a density of 0.875 g/ml and a viscosity of 20.3 cP (25° C.). Gas layer chromatography analysis of this material identified 60% tris(trimethylsiloxy)n-octylsilane, 25% tetrakis (trimethylsiloxy)-1,3-di-n-octyldisiloxane, 9% pentakis (trimethylsiloxy)-1,3,5-tri-n-octyltrisiloxane and 4% higher oligomers.

EXAMPLE 4

The 128 g sample of the product of Example 3 was distilled under vacuum to yield 70 g (55%) of tris (trimethylsiloxy)n-octylsilane, bp 99° C. (1 mm), refractive index 1.410 (25° C.), density 0.84 g/ml (25° C.) and viscosity 3.2 cP (25° C.). GC analysis of this product indicated the purity >97%, the remainder being tetrakis (trimethylsiloxy)-1,3-di-n-octyldisiloxane.

EXAMPLE 5

Sensory characterization was performed on 4 organosilicone samples according to the protocol of ASTM Method E 1490-2, entitled "Sensory Evaluation of Materials and Products." The number of trained test panelists was 15 and the materials used were the following:

1. Tris(trimethylsiloxy)-n-octylsilane, >97% pure
2. Tris(trimethylsiloxy)phenylsilane, >99% pure
3. A mixture of $Me_3SiO(Me_3SiO—n-OctylSiO)_xSiMe_3$ with x=1,2,3 and viscosity of 20 cP (25° C.) from Example 1
4. A mixture of $Me_3SiO(Me_3SiOPhSiO)_xSiMe_3$ with x=1, 2,3 and viscosity of 20 cP (25° C.) prepared by a process analogous to Example 1, but using phenyltrichlorosilane in place of n-octyltrichlorosilane.

Figure 2:
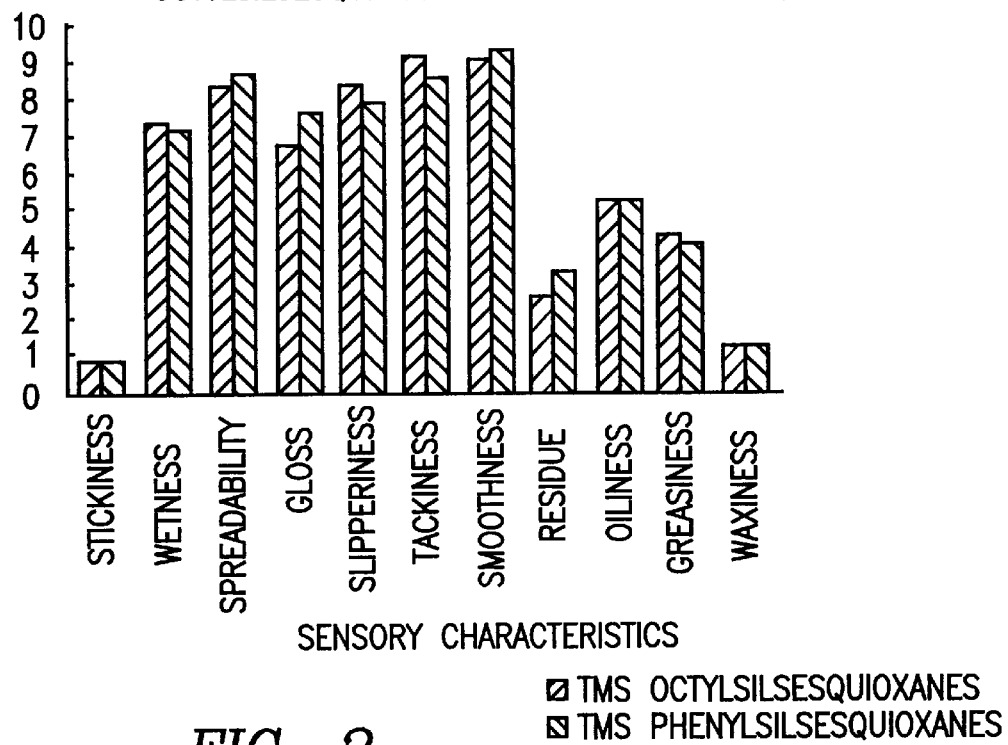
FIG. 2 depicts in bar graph form a sensory comparison of a polymeric mixture of branched alkylsilsesquioxanes of the present invention with an analogous polymeric mixture of phenylsilsesquioxanes.

Subsequent to the testing, the results were tabulated and averaged. The results for compounds 1 and 2 are compared in FIG. 1, while the results for the polymeric mixtures 3 and 4 are compared in FIG. 2.

Within the experimental error associated with this type of testing it can be concluded that the sensory profile of the compounds listed above as 1 and 2 are identical. In the same context, the sensory profile of the polymeric mixtures listed above as 3 and 4 are also identical. Considering the differences between the aromatic vs. aliphatic substitution in these pairs of materials, the results are unexpected.

Many variations of the present invention will suggest themselves to those skilled in the art in light of the above-detailed description. For example, the molar ratio of trimethylchlorosilane to n-octyltrichlorosilane may be varied between 1 and 6. Other monovalent hydrocarbon substituted trichlorosilanes may be employed as a reactant, and mixtures of monovalent hydrocarbon substituted trichlorosilanes may be employed. Additionally, acid catalysts other than sulfuric acid may be employed. All such obvious modifications are within the full intended scope of the appended claims.

All of the above-referenced patents, patent applications, test methods and publications are hereby incorporated by reference.

We claim:

1. A high purity, neutral, colorless and odorless branched alkylsilsesquioxane fluid of the general formula:

$Me_3SiO—(Me_3SiORSiO)_x—SiMe_3$ wherein Me is methyl, R comprises a monovalent aliphatic hydrocarbon substituent having from 6 to 14 carbon atoms, and x ranges from 1 to about 6, said fluid being greater than 97% free of alkoxysilane, chlorosilane, silanol functionality, hexamethyldisiloxane and free organic and/or inorganic compounds.

2. A high purity branched alkylsilsesquioxane fluid as defined in claim 1 wherein x ranges from 1 to 3.

3. A high purity branched alkylsilsesquioxane fluid as defined in claim 1 wherein R comprises a monovalent aliphatic hydrocarbon substituent with 8 carbon atoms.

4. A high purity branched alkylsilsesquioxane fluid as defined in claim 3 wherein R is n-octyl and x ranges from 1 to 3.

5. A high purity branched n-octylsilsesquioxane fluid as defined in claim 4 wherein x is 1.

6. A high purity branched alkylsilsesquioxane fluid as defined in claim 1 which contains no detectable alkoxysilane, chlorosilane, silanol functionality, hexamethyldisiloxane, free organics, and free inorganics.

7. A silicone fluid consisting of tris(trimethylsiloxy)-n-octylsilane.

8. A process for the production of a high purity branched alkylsilsesquioxane fluid of the general formula

$Me_3SiO—(Me_3SiORSiO)_x—SiMe_3$ wherein Me is methyl, R is a monovalent aliphatic hydrocarbon substituent having from 6 to 14 carbon atoms, and x ranges from 1 to about 6, said fluid being greater than 97% free of alkoxysilane, chlorosilane, silanol functionality, hexamethyldisiloxane, free organic compounds and free inorganic compounds, said process comprising the steps of:

(a)
  (i) hydrolyzing a mixture of pure trimethylchlorosilane and pure alkyltrichlorosilane having from 6 to 14 carbon atoms with distilled water in an amount sufficient to produce an aqueous layer of less than about 25 weight percent hydrochloric acid, maintaining the temperature of the hydrolysis reaction mixture below about 90° C., to form a silicone reaction intermediate;
  (ii) washing residual acid from the silicone reaction intermediate; and
  (iii) azeotropically removing water from the washed silicone intermediate to produce a dried silicone reaction intermediate; and (b) trimethylsilylating the silanol groups in the dried silicone reaction intermediate with at least a stoichiometric amount of hexamethyldisiloxane in the presence of an acid catalyst.

9. A process as defined in claim 8 wherein a said trimethylsilylating step is carried out with a two fold excess of the stoichiometric amount of hexamethyldisiloxane.

10. A process as defined in claim 8 wherein said hydrolyzing step is carried out at a temperature below about 60° C.

11. A process as defined in claim 8 wherein said hydrolysis step is carried out with distilled water in an amount sufficient to produce an aqueous layer of from about 15 to about 18 weight percent hydrochloric acid.

12. A process as defined in claim 8 wherein hexamethyldisiloxane is present both at the beginning and the end of the trimethylsilylating step.

13. A process as defined in claim 8 wherein said acid catalyst comprises trifluoromethanesulfonic acid.

14. A process as defined in claim 8 wherein said acid catalyst comprises sulfuric acid.

15. A process as defined in claim 8 wherein said acid catalyst is neutralized and the salt filtered after completion of the trimethylsilylation reaction.

16. A process as defined in claim 12 wherein excess hexamethyldisiloxane present at the end of the trimethylsilylating step is removed from the product by stripping under vacuum.

17. A process as defined in claim 16 wherein said removed hexamethyldisiloxane is recycled to the hydrolysis reaction mixture.

18. A process as defined in claim 8 wherein said washing step is performed to provide a silicone reaction intermediate having a pH of at least 6.

19. A process as defined in claim 8 wherein said alkyltrichlorosilane comprises n-octyltrichlorosilane.

20. A high purity branched alkylsilsesquioxane fluid produced by the process as defined in claim 8.

21. A high purity branched n-octylsilsesquioxane fluid produced by the process as defined in claim 20.

22. A cosmetic formulation comprising a high purity branched alkylsilsesquioxane fluid of the general formula:

$Me_3SiO—(Me_3SiORSiO)_x—SiMe_3$ wherein Me is methyl, R is n-octyl, and x ranges from 1 to 3, said fluid being greater than 99% free of alkoxysilane, chlorosilane, silanol functionality, hexamethyldisiloxane and free organic and/or inorganic compounds.

* * * * *